United States Patent
Mary Lynne et al.

(10) Patent No.: US 6,951,741 B2
(45) Date of Patent: *Oct. 4, 2005

(54) HOST/VECTOR SYSTEM FOR EXPRESSION OF MEMBRANE PROTEINS

(75) Inventors: Collins P. Mary Lynne, Milwaukee, WI (US); Yongjian S. Cheng, Shorewood, WI (US)

(73) Assignee: WiSys Technology Foundation, Inc., Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 10/692,889

(22) Filed: Oct. 24, 2003

(65) Prior Publication Data

US 2004/0086969 A1 May 6, 2004

Related U.S. Application Data

(63) Continuation of application No. 09/660,176, filed on Sep. 12, 2000, now Pat. No. 6,680,179.
(60) Provisional application No. 60/153,576, filed on Sep. 13, 1999.

(51) Int. Cl.[7] ............................ C12P 21/00; C12N 1/21; C12N 15/63
(52) U.S. Cl. ................. 435/69.1; 435/252.3; 435/320.1
(58) Field of Search ............................ 435/69.1, 252.3, 435/320.1; 530/350; 514/12

(56) References Cited

U.S. PATENT DOCUMENTS 6,465,216 B2    10/2002   Laible et al.
6,680,179 B1 *   1/2004   Perille-Collins et al. ... 435/69.1

OTHER PUBLICATIONS

J. Berard, et al., "Mapping of the puh Messenger RNAs from *Rhodospirillum rubrum*," J. Biol. Chem. 264(18):10897–10903, 1989.

J. Berard and G. Gingras, "The puh Sturctural Gene Coding for the H Subunit of the *Rhodospirillum rubrum* Photoreaction Center," Biochem. Cell Biol. 69:122–131, 1991.

J.M. Blatny, et al., "Construction and use of a Versatile Set of Broad–Host–Range Cloning and Expression Vectors Based on the RK2 Replicon," Appl. Env. Microbiol. 63(2):370–379, 1997.

(Continued)

Primary Examiner—Jon Weber
Assistant Examiner—Robert B. Mondesi
(74) Attorney, Agent, or Firm—Quarles & Brady LLP

(57) ABSTRACT

A method of expressing proteins is disclosed. In a preferable embodiment, the method comprises placing a DNA sequence encoding a protein or peptide and expression vector containing a regulatable promoter expressible in *Rhodospirillum rubrum* and expressing the protein within a bacterial host, wherein the host has extra capacity for membrane formation and wherein the host is a member of the genus *Rhodospirillum*.

8 Claims, 4 Drawing Sheets

OTHER PUBLICATIONS

Figure 2:
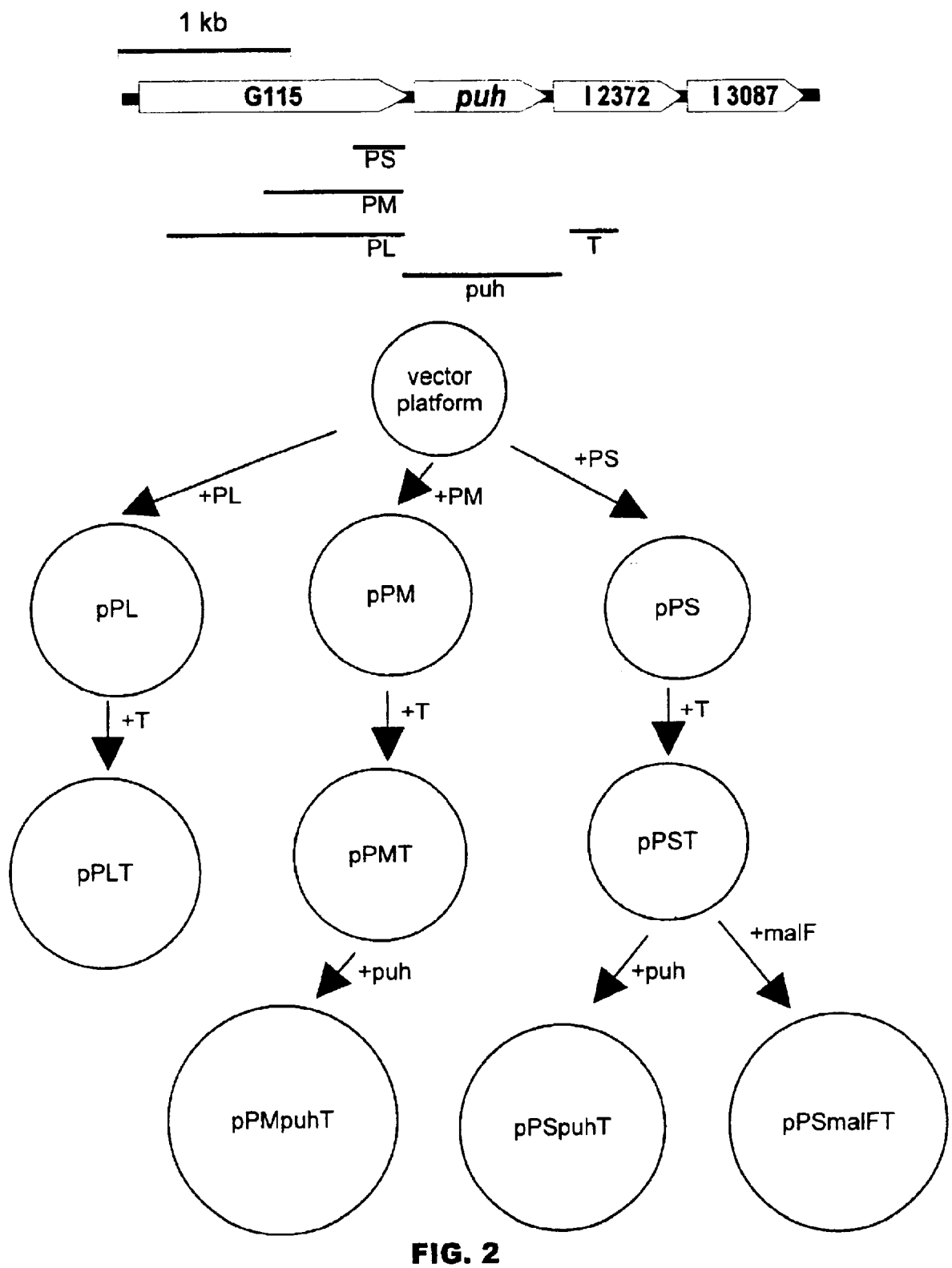

Y.S. Cheng, "Molecular Analysis of Bacterial Intracytoplasmic Membrane Proteins," pp. 1–97, 1998 (Thesis).

Y.S. Cheng, et al., "Role of the H Protein in Assembly of the Photochemical Reaction Center and Intracytoplasmic Membrane in *Rhodospirillum rubrum*," J. Bacteriol. 182(5):1200–1207, 2000.

S.K. Grunwald, et al., "Postranslational Regulation of Nitrogenase in *Rhodospirillum rubrum* Strains Overexpressing the Regulatory Enzymes Dinitrogenase Reductase ADP–robisyltransferase and Dinitorgenase Reductase Activating Glyohydrolase," Am.

M.J. Hessner, et al., "Construction, Characterization, and Complementation of *Rhodospirillum* puf Region Mutants," J. Bacteriol. 173(18):5712–5722, 1991.

B.C. Jester, "Construction and Characterization of a puf Null Mutant of *Rhodospirillum rubrum*," pp. 1–45, 1998 (Thesis).

N.T. Keen, et al., "Improved Broad–Host–Range Plasmids for DNA Cloning in Gram–negative Bacteria," Gene 70:191–197, 1988.

W.R. Jones, et al., "Mutants of *Rhodobacter sphaeroides* Lacking One or More Pigment–Protein Complexes and Complementation with Reaction–Centre, LH1, and LH2 Genes," Molec. Microbiol. 6(9):1173–1184, 1992.

I.Y. Lee and M.L.P. Collins, "Identification and Partial Sequence of the BchA Gene of *Rhodospirillum rubrum*," Curr. Microbiol. 27:85–90, 1993.

* cited by examiner

```
                  Pvu II
                  |
CAGCTGGCGAAAGGGGGATGTGCTGCAAGGCGATTAAGTTGGGTAACGCCAGGGTTTTCCCAGTCACGAC
|----|----|----|----|----|----|----|----|----|----|----|----|----|----| 70
                    EcoR I
                    |
GTTGTAAAACGACGGCCAGTGAATTCGGTGGGCACGCTGACCGCGGCGATGGCGCTGGCCGATGAAACGG
|----|----|----|----|----|----|----|----|----|----|----|----|----|----| 140

TCAGCGGAATGGCGCTCGGCGCTTGGGGCGCCGTGCAGGCCACCGCGACCGGCGCGGCCGTTGCCCTTGG
|----|----|----|----|----|----|----|----|----|----|----|----|----|----| 210

CGGCGGCTTGCGCGATGGCGTTTCCTCGTTGGCGGCCCATGGCCTGCTCGGCGAGGCCTTAACCACGGCC
|----|----|----|----|----|----|----|----|----|----|----|----|----|----| 280

CATACGGGCTATGGTTTCGTTTATCTGGTAGAAGTTGTTTTGTTATTTACAACCTTGGCCATCATCGGCC
|----|----|----|----|----|----|----|----|----|----|----|----|----|----| 350

CGCTCGTTCGTACGGCCGGACACCGCGCGTCCCAGTCTTCGGAAGGACGTTTCGGTTTGGCCGAGTTCCC
|----|----|----|----|----|----|----|----|----|----|----|----|----|----| 420
             Kpn I
             |Sma I
             ||
       Sac I || BamH I Xba I Sal I    Pst I   Sph I
       |     ||| |     |     |        |       |
AGGAGAGCTCGGTACCCGGGGATCCTCTAGAGTCGACCTGCAGGCATGCCACATGGATGAGTACGATTCC
|----|----|----|----|----|----|----|----|----|----|----|----|----|----| 490
                                EcoR I
                                |
GAACCGATCCGTGGACTGCCTGCGGATCTGCCGCCGGGCGAATTCATCCTGTGGCAGGGCGCGCCGACAC
|----|----|----|----|----|----|----|----|----|----|----|----|----|----| 560

GGCGCGCCCTTGCCCTCCGGGTGTTTCACATTCGGCTGATCGCGCTTTATTTCGCGATTCTGGTGGCGTG
|----|----|----|----|----|----|----|----|----|----|----|----|----|----| 630
                            Hind III
                            |
GAACGTGGCCTCGGCTTTGTATGACGGCCATCCGCTGCCCAAGCTTGGCGTAATCATGGTCATAGCTGTT
|----|----|----|----|----|----|----|----|----|----|----|----|----|----| 700

TCCTGTGTGAAATTGTTATCCGCTCACAATTCCACACAACATACGAGCCGGAAGCATAAAGTGTAAAGCC
|----|----|----|----|----|----|----|----|----|----|----|----|----|----| 770

TGGGGTGCCTAATGAGTGAGCTAACTCACATTAATTGCGTTGCGCTCACTGCCCGCTTTCCAGTCGGGAA
|----|----|----|----|----|----|----|----|----|----|----|----|----|----| 840
       Pvu II
       |
ACCTGTCGTGCCAGCTG
|----|----|-----> 857
```

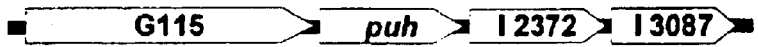

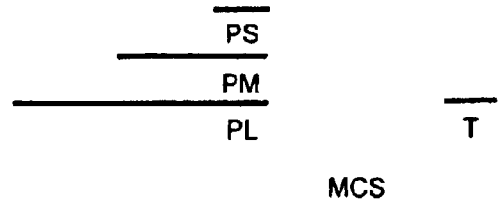

FIG. 1

SEQUENCE LISTING

<160> NUMBER OF SEQ ID NOS: 8

<210> SEQ ID NO 1
<211> LENGTH: 857
<212> TYPE: DNA
<213> ORGANISM: Artificial Sequence
<220> FEATURE:
<223> OTHER INFORMATION: Description of Artificial Sequence:expression
      vector
<220> FEATURE:
<221> NAME/KEY: misc_feature
<222> LOCATION: (430)..(468)
<223> OTHER INFORMATION: Multiple cloning site
<220> FEATURE:
<221> NAME/KEY: misc_feature
<222> LOCATION: (92)..(429)
<223> OTHER INFORMATION: PS fragment
<220> FEATURE:
<221> NAME/KEY: misc_feature
<222> LOCATION: (469)..(671)
<223> OTHER INFORMATION: T fragment

<400> SEQUENCE: 1
cagctggcga aaggggggatg tgctgcaagg cgattaagtt gggtaacgcc agggttttcc      60
cagtcacgac gttgtaaaac gacggccagt gaattcggtg gcacgctga ccgcggcgat      120 ggcgctggcc gatgaaacgg tcagcggaat ggcgctcggc gcttggggcg ccgtgcaggc     180
caccgcgacc ggcgcggccg ttgcccttgg cggcggcttg cgcgatggcg tttcctcgtt     240
ggcggcccat ggcctgctcg gcgaggcctt aaccacggcc catacgggct atggtttcgt     300
ttatctggta gaagttgttt tgttatttac aaccttggcc atcatcggcc cgctggttcg     360
tacggccgga caccgcgcgt cccagtcttc ggaaggacgt ttcggtttgg ccgagttccc     420
aggagagctc ggtacccggg gatcctctag agtcgacctg caggcatgcc acatggatga     480
gtacgattcc gaaccgatcc gtggactgcc tgcggatctg ccgccgggcg aattcatcct     540
gtggcagggc gcgccgacac ggcgcgccct tgccctccgg gtgtttcaca ttcggctgat     600 cgcgcttttat ttcgcgattc tggtggcgtg gaacgtggcc tcggctttgt atgacggcca     660
tccgctgccc aagcttggcg taatcatggt catagctgtt tcctgtgtga aattgttatc     720
cgctcacaat tccacacaac atacgagccg gaagcataaa gtgtaaagcc tggggtgcct     780
aatgagtgag ctaactcaca ttaattgcgt tgcgctcact gcccgctttc cagtcgggaa     840
acctgtcgtg ccagctg                                                    857

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
gtaattgggg gcatgccaca tggatga                                          27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence:
      oligonucleotide -continued

```
<400> SEQUENCE: 3
cggcggtcag aagcttgggc agcggat                                              27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
gcaaccaagg aattcccgct gggtcgt                                              27

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
gagggtgacg agctctcctg ggaactc                                              27

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
atgaccagtt gagctcccat ccagccgctt gg                                        32

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
gttcccagga gagctcgtca ccctcag                                              27

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 8
gcgcggtgcg catgccttag atcgcgacgg catc                                      34
```

HOST/VECTOR SYSTEM FOR EXPRESSION OF MEMBRANE PROTEINS

CROSS-REFERENCE TO RELATED APPLICATION

This application is a continuation of U.S. Ser. No. 09/660,176, filed Sep. 12, 2000 now U.S. Pat. No. 6,680,179 which claims priority to Ser. No. 60/153,576 filed Sep. 13, 1999. Both Ser. No. 60/153,576 and U.S. Ser. No. 09/660,176 are incorporated by reference herein.

STATEMENT REGARDING FEDERALLY SPONSORED RESEARCH OR DEVELOPMENT

This invention was made with United States government support awarded by the following agencies: NIH GM57322. The United States has certain rights in this invention.

BACKGROUND OF THE INVENTION

*Rhodospirillum rubrum* is a facultatively phototrophic purple nonsulfur bacterium. Under reduced oxygen concentration, this organism forms an intracytoplasmic membrane (ICM) that is the site of the photosynthetic apparatus (Collins, M. L. P., and C. C. Remsen, *The purple phototrophic bacteria*, p. 49–77, In J. F. Stolz (ed.), Structure of Phototrophic Procaryotes. CRC Press, Boca Raton Fla., 1990; Crook, S. M., et al., *J. Bacteriol.* 167:89–95, 1986; Hessner, M. J., et al., *J. Bacteriol.* 173:5712–5722, 1991). This apparatus consists of the light-harvesting antenna (LH) and the photochemical reaction center (RC). The pigment-binding proteins, the LH $\alpha$ and $\beta$ and the RC-L and -M, are encoded by the puf operon while RC-H is encoded by puhA. The nucleotide sequences of puhA and the puf operon have been determined in *R. rubrum* (Bélanger, G., et al., *J. Biol. Chem.* 263:7632–7638, 1988; Bérard, J., et al., *J. Biol. Chem.* 261:82–87, 1986; Bérard, J., and G. Gingras, *Biochem. Cell Biol.* 69:122–131, 1991) and related bacteria (Donohue, T. J., et al., *J. Bacteriol.* 168:953–961, 1986; Kiley, P. J., et al., *J. Bacteriol.* 169:742–750, 1987; Michel, H., et al., *EMBO J.* 5:1149–1158, 1986; Michel, H., et al., *EMBO J.* 4:1667–1672, 1985; Weissner, C., et al., *J. Bacteriol.* 172:2877–2887, 1990; Williams, J. C., et al., *Proc. Natl. Acad. Sci.* 81:7303–7307, 1984; Williams, J. C., et al., *Proc. Natl. Acad. Sci.* 80:6505–6509, 1983; Youvan, D. C., et al., *Proc. Natl. Acad. Sci.* 81:189–192, 1984; Youvan, D. C., et al., *Cell* 37:949–957, 1984).

*R. rubrum* may grow phototrophically under anaerobic light conditions or by respiration under aerobic or anaerobic conditions in the dark. Because *R. rubrum* is capable of growth under conditions for which the photosynthetic apparatus is not required, and because the photosynthetic apparatus and the ICM may be induced by laboratory manipulation of oxygen concentration, this is an excellent organism in which to study membrane formation (Collins, M. L. P., and C. C. Remsen, supra, 1990; Crook, S. M., et al., supra, 1986).

In previous studies, the puf region was cloned and interposon mutations within this region were constructed (Hessner, M. J., et al., supra, 1991). *R. rubrum* P5, in which most of the puf genes were deleted, was shown to be incapable of phototrophic growth and ICM formation. P5 was restored to phototrophic growth and ICM formation by complementation with puf in trans (Hessner, M. J., et al., supra, 1991; Lee, I. Y., and M. L. P. Collins, *Curr. Microbiol.* 27:85–90, 1993). These results imply that in *R. rubrum* the puf gene products are required for ICM formation. These results differ from those obtained with a puf interposon mutant of *Rhodobacter sphaeroides* (Davis, J., et al., *J. Bacteriol.* 170:320–329, 1988) which was phototrophically incompetent but was still capable of ICM formation (Kiley, P. J., and S. Kaplan, *Microbiol. Rev.* 52:50–69, 1988). In the case of *R. sphaeroides*, the formation of ICM in the absence of the puf products may be attributable to the presence of an accessory light-harvesting component (LHII) encoded by puc (Hunter, C. N., et al., *Biochem.* 27:3459–3467, 1988). This implies that *R. rubrum* is a simpler model for studies of membrane formation.

Because the puf-encoded proteins are required for ICM formation in *R. rubrum* and because the RC is assembled from puf and puhA products, it is important to evaluate the role of puhA-encoded RC-H in RC assembly and ICM formation in *R. rubrum*.

Cheng, et al., *J. Bacteriol.* 182(5):1200–1207, 2000 and Yongjian S. Cheng, "Molecular Analysis of Biochemical Intracytoplasmic Membrane Proteins," PhD thesis, UW-Milwaukee, August, 1998 describe the cloning, mutation, and complementation of the puhA region of *R. rubrum*. (Both of these documents are incorporated herein by reference.) The present application proposes a model for the preparation of proteins, preferably membrane proteins.

SUMMARY OF THE INVENTION

In one embodiment, the present invention is a method of expressing protein comprising the steps of placing a DNA sequence encoding a protein or peptide in an expression vector that contains a regulatable promoter expressible in *Rhodospirillum rubrum* and expressing the protein within a bacterial host, wherein the host has extra capacity for membrane formation and wherein the host is a member of the genus *Rhodospirillum*.

In a preferred embodiment of the present invention, the protein or peptide is a membrane protein or peptide and/or the protein or peptide is a heterologous protein or peptide.

In another preferred form of the present invention, the host is *Rhodospirillum rubrum*.

In another embodiment, the present invention is a protein expression system. In one embodiment, the protein expression system encompasses a vector comprising a DNA molecule encoding the protein or peptide in an expression vector containing a regulatable promoter expressible in *R. rubrum*. The vector is contained within a host, preferably *R. rubrum* with extra capacity for membrane formation.

Other objects, advantages and features of the present invention will become apparent to one of skill in the art after review of the specification, claims and drawings.

DETAILED DESCRIPTION OF THE SEVERAL VIEWS OF THE DRAWINGS

FIG. 1 is a diagram illustrating the construction of the expression cassettes and the DNA sequence of the cassette of pREX1 (SEQ ID NO:1). The PS fragment extends from position 92–429 and the T fragment extends from position 469–671. The multiple cloning site is from position 430–468. Sequences from position 1–91 and 672–857 are those of the vector. PM, PL and PG are not shown and include additional upstream sequences. The exact lengths and positions of PS/PM, PL and PG are specified by the sequences of the primers reported herein and in Cheng thesis, supra.

FIG. 2 diagrams the construction of various expression vectors. PCR products PS, PM, PL and PG (not shown) from the various puh regions are shown in position and size relative to the map of puh and flanking ORFs.

Figure 3:
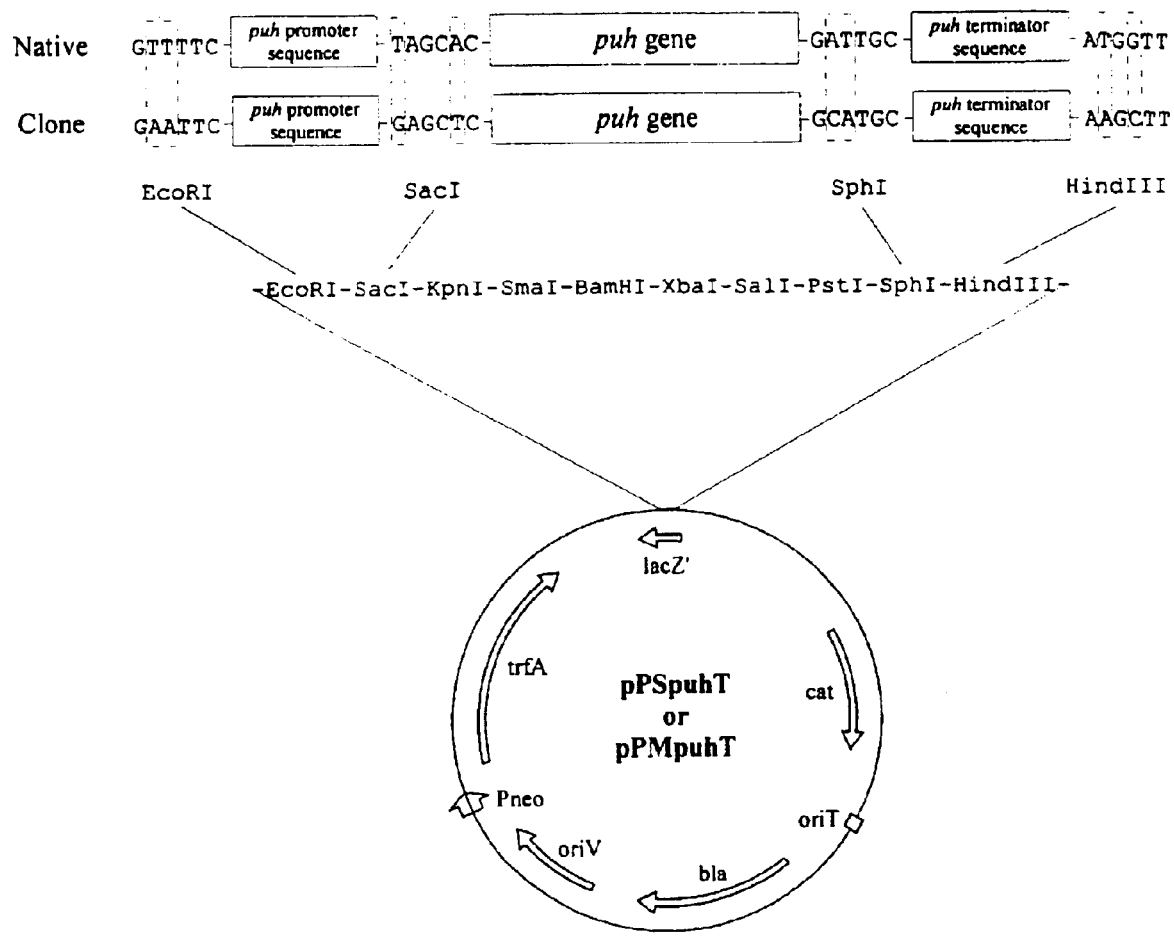

FIG. 3 is a diagram of modular cloning of pPSpuhT or pPMpuhT. PCR primers incorporated appropriate restriction sites to facilitate cloning of pPSpuhT or pPMpuhT. The promoter and terminator sequences were placed at the ends of the multiple cloning site to allow flexibility in designing PCR primers for cloning genes inserted between the promoter and terminator. Mutated bases are indicated by the dotted boxes.

Figure 4:
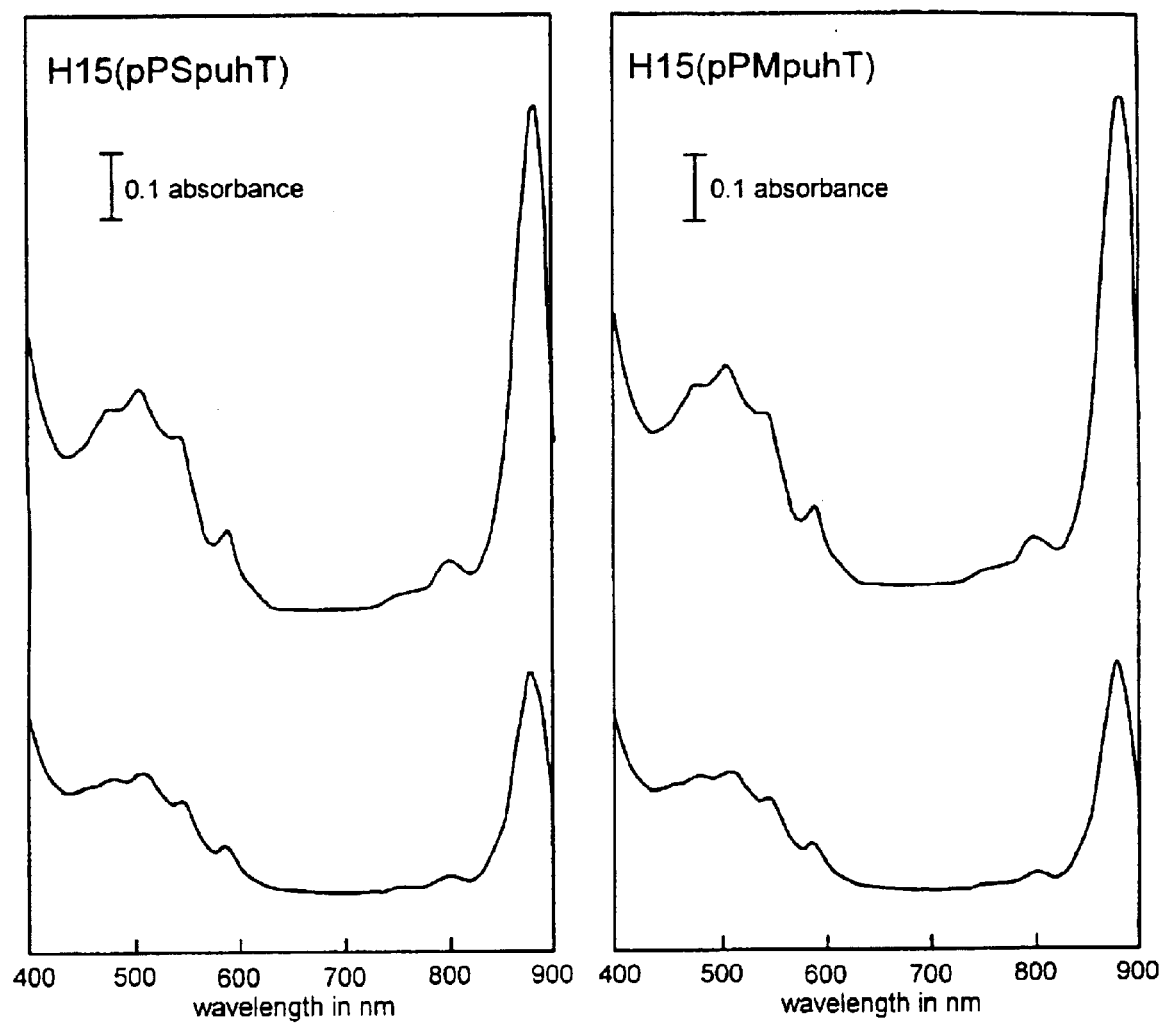

FIG. 4 is a set of absorbance spectra of *R. rubrum* H15 complemented with pPSpuhT and pPMpuhT. Cells were grown phototropically (top of spectra) or semi-aerobically (bottom of spectra).

DESCRIPTION OF THE INVENTION

In one embodiment, the present invention is a host/vector system for expression of proteins. In preferable embodiments of the present invention, the protein is a heterologous protein and/or a membrane protein. While numerous expression vector systems are commercially available, these vector systems generally cannot be applied to membrane proteins. Over-expression of membrane proteins is often toxic for the cell or results in the production of inclusion bodies in which the protein is in a non-native structure.

By "membrane proteins" we mean proteins normally or naturally located in the cell membrane. Such proteins generally have one or more membrane-spanning domains.

A host designed for the expression of membrane proteins in the present invention should have extra capacity to proliferate membranes to accommodate the expressed protein. Extra capacity would avoid problems with formation of inclusion bodies or lethality associated with over-expressed membrane proteins. By "extra capacity" we mean that the host organism has the ability to make an intracytoplasmic membrane (ICM) but has a reduced ability to produce native membrane proteins.

The ability of a bacterium to make an ICM can be determined (assayed) by examining a sample with the electron microscope. ICM is known to be made ordinarily by only three known groups of bacteria—phototrophs (such as *R. rubrum*), methanotrophs and ammonia-oxidizers. The latter two (especially ammonia-oxidizers) are not preferred for molecular biology applications because of their growth requirements.

The extra capacity for ICM formation by the mutants described herein is due to mutation in the genes encoding the major membrane proteins—i.e., the proteins of the photochemical complexes. Because the bacteria retain the capacity to make ICM, they have "extra capacity."

The host is a member of the genus *Rhodospirillum* and most preferably one of several mutants of *Rhodospirillum rubrum*. Preferably, the mutant hosts are defective in the production of puhA-encoded RC-H (*Rhodospirillum rubrum* H15) or puhA-encoded RC-H and puf-encoded LH-α, LH-β, RC-L and RC-M (*Rhodospirillum rubrum* H1). A puf knock-out mutant (*Rhodospirillum rubrum* P5 or P4) would also be suitable. (Note that P5 mutant has a puf phenotype but still retains a partial pufB but pufALM is completely deleted.) Another puf mutant, *R. rubrum* P4 (described in Jester, B., MS Thesis, University of Wisconsin at Milwaukee, May 1998, incorporated by reference herein), which is a puf knock-out but differs from P5 in that more genomic DNA is removed, is also suitable.

The basis for the mutational design described herein is that the host's ability to produce its own native major membrane proteins has been disrupted, thus providing the "extra capacity" to incorporate heterologous membrane proteins. For *R. rubrum* this means knocking or disrupting out puh and/or puf. For other phototrophic bacteria (e.g., *Rhodobacter sphaeroides*), it would be preferable to also knock out puc which encodes an additional photochemical component that is a major membrane protein. Such an *R. sphaeroides* mutant has been constructed (see M. R. Jones, et al., *Molec. Microb.* 6:1173–1184, 1992).

While these *R. rubrum* mutants are impaired in ICM formation, they retain the capacity to form an intracytoplasmic membrane in response to the synthesis of membrane proteins, including heterologous membrane proteins. (Cheng, et al., supra, 2000, describes a comparison of the properties of wild-type *Rhodospirillum rubrum* and mutated *Rhodospirillum rubrum* and describes the development of a suitable host for the present invention. (This article is incorporated by reference as if fully set forth herein.) In addition, Cheng, et al., supra, 2000, reports that the puh promoter is contained within pH 3.6+. This promoter is incorporated into the expression vector described herein and is derepressed (i.e., induced) by semi-aerobic conditions.

The *R. rubrum* system is advantageous, in part, because *R. rubrum* does not infect humans or animals and grows on a simple medium. The intracytoplasmic membrane that houses the expressed protein may be separated from the other particulate cellular material.

One may most easily obtain a suitable *R. rubrum* host by constructing organisms analogous to P5 or H15. P5 may be reconstructed by following Hessner, et al., supra, 1991. H15 may be reconstructed by following the procedure of Cheng, et al., supra, 2000.

An expression vector of the present invention should have the following properties: (a) strong promoter; (b) regulated promoter; and (c) promoter regulated by a stimulus that is simple, inexpensive and non-toxic. The parent plasmid used to construct the expression vector must be capable of replication in a *R. rubrum* host. We have used IncP plasmids to construct the expression vector. However, IncQ plasmids also replicate in *R. rubrum*, and one preferred embodiment of the present invention would be to move the cassette into an IncQ plasmid. Because these plasmids would be compatible in the host, this will make it possible to simultaneously express two proteins. This embodiment could be applied to the synthesis of a membrane protein that is a heterodimer. Alternatively, it may be possible to use a single vector to express oligomeric proteins that are co-transcribed on a single message.

The expression vectors preferably include an *R. rubrum* promoter which can be induced by reduction of oxygen. In addition, to being able to replicate in the *Rhodospirillum rubrum* host, the expression vector must have a promoter that is expressed strongly in this host.

Our development of a suitable expression vector is based on our studies of puh expression. The expression vector pREX1 (also known as pPST) is a construct in which cloning sites are located between promoter and terminator sequences.[1] These sequences are derived from the puh region of pH 3.6+/−. The expression vectors pREX2 (also known as pPMT) and pREX3 (also known as pPLT, not yet built) contain longer portions of the *R. rubrum* sequence contained within pH 3.6−. The promoter can be induced by reduction of oxygen tension. When the gene encoding a desired protein, such as a membrane protein, is cloned into this expression vector and the vector is introduced into a suitable host, such as *Rhodospirillum rubrum* H15 or *Rho-* dospirillum rubrum H1, this protein can be expressed by reducing the oxygen tension. This expression has been demonstrated by the expression of *Escherichia coli* MaIF in *Rhodospirillum rubrum* H15, as described below in the Examples.

[1] Applicants note that some nomenclature regarding expression vectors and clones has been modified between the Cheng PhD thesis (Yongjian S. Cheng, "Molecular Analysis of Biochemical Intracytoplasmic Membrane Proteins," UW-Milwaukee, August 1998), priority application U.S. Ser. No. 60/153,576, Cheng, et al., supra 2000 and the present application. The table below describes the relationship of this terminology.

The construct pH 3.6– has a strong promoter which results in the synthesis of mRNA encoding the abundant protein PuhA. This promoter is regulated by oxygen and it can be derepressed by simple manipulations applicable to both lab scale and production scale. This avoids the use of chemical inducers which may be costly and/or toxic.

NOMENCLATURE OF EXPRESSION VECTOR AND CLONES

| This application | U.S. Ser. No. 60/153,576 | Cheng thesis |
|---|---|---|
| pREX1, pPST | pPST | pPST |
| pREX2, pPMT | pPLT | pPLT |
| pPREX3, pPLT | — | — |
| pPSpuhT | pPSpuhT | pPSpuhT |
| pPMpuhT | pPLpuhT | pPLpuhT |
| pPSpuh88T | — | pPSHD1T |

FIG. 1 is a diagram illustrating the construction of the expression cassettes and the DNA sequence of the cassette of pREX1. The DNA sequence includes a small portion of the vector sequence that could be used in subcloning a cassette into various vectors. The sequence of the puh region was reported in the literature. (Bérard, J., et al., *J. Biol. Chem.* 264:10897–10903, 1989 and Bérard, J. and Gingras, G, *Biochem. Cell Biol.* 69:122–131, 1991).

We envision the construction of pPLT and pPGT, alternatives with more upstream sequence, as follows:

Longer promoter fragments will be amplified using PF3EcoRI and PF4SacI. (See Table 1 below.) pRK415 will be used as a platform. The PG fragment amplified using PF4SacI contains all of the sequence upstream of puhA in pH 3.6– and extends into the additional sequence reported in Cheng, et al., supra, 2000.

TABLE 1

Amplification Primers

| | | |
|---|---|---|
| TFSphI | GTAATTGGGGGCATGCCACATGGATGA | (SEQ ID NO:2) |
| TRHindIII | CGGCGGTCAGAAGCTTGGGCAGCGGAT | (SEQ ID NO:3) |
| PF3EcoRI | GCAACCAAGGAATTCCCGCTGGGTCGT | (SEQ ID NO:4) |
| PRSacI | GAGGGTGACGAGCTCTCCTGGGAACTC | (SEQ ID NO:5) |
| PRSacI | ATGACCAGTTGAGCTCCCATCCAGCCGCTTGG | (SEQ ID NO:6) | pPLT will be constructed with a similar strategy for pPST and pPMT. In brief:
1. One would PCR amplify PL product with PF3EcoRI and PRSacI
2. Digest with EcoRI and SacI or SstI
3. Digest pRK415 Eco and SacI or SstI
4. Ligate PL fragment into digested vector to construct pPL; transform *E. coli*.
5. PCR amplify T fragment with TRHindIII and TFSphI
6. Digest T PCR product with SphI and HindIII
7. Digest pPL with SphI and HindIII
8. Ligate T fragment into digested pPL The strategy for pPGT is similar:
1. PCR amplify T fragment with TR and TF
2. Digest T PCR product with SphI and HindIII
3. Digest pRK415 with SphI and HindIII
4. Ligate T fragment into digested pRK415 to form pRKT
5. PCR amplify PG product with Pf4SacI and PRSacI
6. Digest pRKT with SacI
7. Ligate PG fragment into SacI-digested pRKT
8. Transform *E. coli* and screen transformants to identify those with the PG sequence in the correct orientation.

Applicants deposited strain *Rhodospirillum rubrum* H1 at ATCC (10801 University Boulevard, Menassas, Va. 20110-2209) Patent Deposit designation PTA-5207 under the terms and conditions of the Budapest Treaty. Access to the deposit will be available during the pendency of the patent application to one determined by the Commissioner to be entiteled thereto under 35 U.S.C. § 1.14 and 35 U.S.C § 122. Subject to 37 C.F.R. § 1.808(2) (b), all restrictions imposed by the depositor on the availability to the public of the deposited material will be irrevocably removed up on granting of the patent.

To build a construct that expresses a desired protein, the following steps would preferably be used:

1. Amplify by PCR the structural gene encoding the protein. For this purpose, the PCR primers should incorporate a restriction site available in the polycloning site such that the amplified product can be inserted in the correct orientation. The sites must be in the multiple cloning site and not present in the parent plasmid used to construct the expression vector nor in the structural gene being cloned. The promoter/MCS/terminator sequences (FIG. 1) can be subcloned into different parent plasmids and this will affect the sites available for cloning. Primers may incorporate an optimized ribosomal binding site. To clone a partial sequence, initiation and termination codons as well as a ribosomal binding site preferably should be engineered into the primers. To clone eukaryotic proteins, the template DNA preferably should be cDNA in order to avoid introns.

2. Trim the purified PCR product with the appropriate restriction enzymes. It would be possible to use the same restriction site on both primers. However, under these conditions, this will not be "directional cloning" and it will be necessary to screen recombinants (restriction analysis) to identify those in the proper orientation.

3. Ligate the trimmed fragment into the expression vector digested with the appropriate enzymes. In addition to pJB3Cm6 (mentioned in the Examples), other vectors that could preferably be used as a platform for the expression fragment are pSUP104, pJRD215 and pKT210. (See [for pPSUP104]: Priefer, U. B., et al., *J. Bacteriol.* 163:324–330, 1985; [for pJRD215]: Davison, J., et al., *Gene* 51:275–280, 1987; [for pKT210]: Priefer, U. B., et al., *J. Bacteriol.* 163:324–330, 1985.)

4. Transform a suitable *E. coli* strain (such as S17-1) with the construct.

5. Conjugate the construct into the *R. rubrum* host. Alternatively, *R. rubrum* can be electroporated or transformed. Select for transconjugants with the appropriate antibiotic. The appropriate antibiotic will be determined by the selection markers on the parent plasmid and the host.

6. Culture transconjugant under aerobic conditions.

7. Reduce oxygen tension to derepress cloned gene under control of puh promoter.

There are numerous potential applications for the host/vector system of the present invention. For example, biotechnology investigators could use the system in basic science applications concerning the numerous putative genes that have been identified and continue to be identified by genome sequencing. Immunological and biochemical approaches to understanding the role of these genes in healthy and diseased cells will require expression of the genes. This new host/vector system is uniquely suited for expression of membrane proteins.

Physical analysis (e.g. X-ray crystallography) requires milligram quantities of pure protein. This requirement has limited the application of this type of analysis to only a few membrane proteins, largely those that are highly expressed in their natural host. Expression of membrane proteins in the new host/vector system would extend this approach to many membrane proteins of importance. This would include, for example, receptors which play a role in intercellular communication in the immune response, neuroendocrine function, viral infection, and other important physiological activities.

Many immunoprotective antigens of viruses, bacteria and other infectious agents are membrane proteins. One of the most important potential applications of the present invention would be to produce vaccines. This host/vector system could be used for the production of new, improved or more cost-effective subunit vaccines. Among the potential advantages of this system are the following: (1) vaccine would not be infectious, (2) large scale production should be efficient, (3) proteins from difficult-to-cultivate pathogens could be expressed provided that sufficient sequence information is available to design PCR primers, and (4) the protein should be assembled in the membrane in its native (antigenic) state.

One potential obstacle is that the expressed protein would not be modified as in the native host. In the case of modification by proteolytic cleavage, this obstacle may be overcome by engineering a truncated protein. Viral proteins that are normally glycosylated would not be modified when produced in this R. rubrum host/vector system. However, non-glycosylated proteins may stimulate the production of protective antibody as has been found to be the case with the recombinant vaccine now in use for hepatitis B.

EXAMPLES

Vectors designed for the expression of membrane proteins in R. rubrum H15 were constructed. These constructs were based on pJB3Cm6 because this vector is small and fully sequenced. See, Blatny, J. M., et al., Appl. Environ. Microb. 63:370–379, 1997. Also note, the sequence of the puh region is reported in Bérard, J., et al., supra, 1989 and Bérard, J. and Gingras, G, supra, 1991. Expression of cloned genes will be driven by puh expression sequences contained within pH 3.6–. Because of uncertainty in the length of sequence required for oxygen regulated expression, four putative puh promoter sequences of differing length (designated S and M done, L and G in progress) will be amplified by PCR and cloned into this vector to form pPS, pPM, pPL and pPG (FIG. 2). The putative puh terminator sequence was or will be cloned into each of these to form pPST, pPMT, pPLT and pPGT (FIG. 2). These sequences flank multiple cloning sites into which genes intended for expression may be cloned.

To test the capacity to express genes, the homologous gene puhA was used as a reporter. PuhA was amplified by PCR using primers that incorporated restriction sites for SacI and SphI. The PCR product and the vectors were treated with these enzymes and the PCR fragments were ligated to the vectors to form pPSpuhT and pPMpuhT (FIGS. 2 and 3). These constructs were used to transform Escherichia coli S17-1 that was in turn conjugated to the puh knock-out strain R. rubrum H15. Both pPSpuhT and pPMpuhT restored phototrophic growth and photopigment content to H15 and the photochemical reaction center was detected by spectroscopy in cells incubated under phototrophic or semi-aerobic conditions (FIG. 4). The vector controls (pPST and pPMT) did not restore the phenotype. These results suggest that both expression vectors will function in R. rubrum for puhA expression.

To test the expression of a heterologous protein, MaIF was amplified by PCR using total DNA from E. coli MC4100 as a template. This PCR product was cloned into pPST to form pPSMaIFT (FIG. 2). This plasmid was transferred to R. rubrum H15 by conjugation and H15 (pPSMaIFT) was incubated under semi-aerobic conditions to evaluate expression of maIF. Membranes were prepared from H15(pPSMaIFT) and H15(pPSpuhT); the latter served as a negative control. When analyzed by SDS-PAGE, MaIF was not detected (not shown). When analyzed by immunoblot, MaIF was detected in membranes prepared from H15(pPSMaIFT) but not H15(pPSpuhT). These results indicate that while expression of MaIF was achieved, hyperexpression was not.

Use of pREX to Express a Truncated Protein

The expression of puhA from pREX (aka pPST) provided the opportunity to evaluate a truncated puhA. The reverse primer 88R (below) was designed to incorporate a termination codon as well as a restriction site. The fragment amplified with HF and 88R, which encodes the first 88 amino acids of RC-H, was cloned into pREX to form pREXpuh88. The phenotype of H15 complemented with this construct was evaluated. This truncated puhA restored the photopigment content of the membrane to a level equivalent to that obtained with pREXpuh which is reflected in the spectrum. The spectrum also shows a peak at 800 nm indicative of the photochemical reaction center (RC). This RC formed with a truncated RC-H is functional because H15 (pREXpuh88) is capable of phototrophic growth. The ability to grow phototrophically was lost when H15 was cured of pREXpuh88.

HF    GTTCCCAGGAgAGCtCGTCACCCTCAG       (SEQ ID NO:7)
                    SacI (SEQ ID NO:8)
88R   GCGCGGTGCGCaTGcCTTaGATCGCGACGGCATC[3]
           SphI restrictions sites in bold
termination codon underlined

We claim:

1. A method of expressing proteins comprising the steps of
   (a) placing a DNA sequence encoding a protein or peptide in an expression vector comprising a regulatable promoter expressible in *Rhodospirillum rubrum*, wherein the DNA sequence encoding the protein or peptide is operably connected to the promoter, and
   (b) expressing the protein within a bacterial host, wherein the host has extra capacity for membrane formation and wherein the host is a member of the genus *Rhodospirillum*.

2. The method of claim 1 wherein the protein or peptide is a membrane protein or peptide.

3. The method of claim 1 wherein the protein or peptide is a heterologous protein or peptide.

4. The method of claim 1 wherein the host is *Rhodospirillum rubrum* P5 or *Rhodospirillum rubrum* P4.

5. The method of claim 1 wherein the expression vector comprises a promoter that can be induced by reduction of oxygen tension.

6. A protein expression system comprising:

a vector comprising a DNA molecule encoding a protein or peptide in an expression vector comprising a regulatable promoter expressible in *R. rubrum*, wherein the vector is contained within a host of the genus *Rhodospirillum* and wherein the host has extra capacity for membrane formation and wherein the DNA molecule encoding the protein or peptide is operably connected to the promoter.

7. The protein expression system of claim 6 wherein the protein or peptide is a heterologous protein or peptide.

8. The protein expression system of claim 6, wherein the protein or peptide is a membrane protein or peptide.

* * * * *

UNITED STATES PATENT AND TRADEMARK OFFICE
CERTIFICATE OF CORRECTION

PATENT NO. : 6,951,741 B2
DATED : October 4, 2005
INVENTOR(S) : Mary Lynne P. Collins and Youngjian S. Cheng It is certified that error appears in the above-identified patent and that said Letters Patent is hereby corrected as shown below:

<u>Title page,</u>
Item [75], Inventors, "Collins P. Mary Lynne" should be -- Mary Lynne P. Collins --.

<u>Column 5,</u>
Line 3, "MaIf" should be -- MalF --.

<u>Column 6,</u>
Lines 26 and 27, "up on grating" should be -- upon granting --.

<u>Column 8,</u>
Lines 17, 25, 27 and 29, "MaIF" should be -- MalF --.
Lines 20, 22, 24 and 28, "pPSMaIFt" should be -- pPSMalFT --.
Line 23, "maIF" should be -- MalF --.

Signed and Sealed this

Thirtieth Day of May, 2006

JON W. DUDAS
*Director of the United States Patent and Trademark Office*

UNITED STATES PATENT AND TRADEMARK OFFICE
CERTIFICATE OF CORRECTION

PATENT NO. : 6,951,741 B2  
APPLICATION NO. : 10/692889  
DATED : October 4, 2005  
INVENTOR(S) : Mary Lynne Perille-Colins and Yongjian S. Cheng Page 1 of 1

It is certified that error appears in the above-identified patent and that said Letters Patent is hereby corrected as shown below:

Column 1, line 15

Replace:
[[This invention was made with United States government support awarded by the following agencies: NIH GM57322. The United States has certain rights in this invention.]]

with:
--This invention was made with government support under GM57322 awarded by the National Institutes of Health. The government has certain rights in the invention.--

Signed and Sealed this  
Eighth Day of November, 2011

David J. Kappos  
*Director of the United States Patent and Trademark Office*

UNITED STATES PATENT AND TRADEMARK OFFICE
CERTIFICATE OF CORRECTION

PATENT NO. : 6,951,741 B2
APPLICATION NO. : 10/692889
DATED : October 4, 2005
INVENTOR(S) : Mary Lynne Perille-Collins et al.

It is certified that error appears in the above-identified patent and that said Letters Patent is hereby corrected as shown below:

In the Specification

Column 1, Line 15:

Replace the following paragraph:   [[This invention was made with government support under GM57322 awarded by the National Institutes of Health. The government has certain rights in the invention.]]

With the paragraph:   --This invention was made with government support under GM057322 awarded by the National Institutes of Health. The government has certain rights in the invention.--

Signed and Sealed this
Twenty-eighth Day of June, 2022

Katherine Kelly Vidal
*Director of the United States Patent and Trademark Office*